US006855324B2

(12) United States Patent
Sandler (10) Patent No.: US 6,855,324 B2
(45) Date of Patent: Feb. 15, 2005

(54) THERAPEUTIC PLACEBO ENHANCEMENT OF COMMONLY-USED MEDICATIONS

(76) Inventor: Adrian Sandler, 316 Covewood Trail, Asheville, NC (US) 28805

( * ) Notice: Subject to any disclaimer, the term of this patent is extended or adjusted under 35 U.S.C. 154(b) by 150 days.

(21) Appl. No.: 09/992,832

(22) Filed: Nov. 16, 2001

(65) Prior Publication Data

US 2002/0061317 A1 May 23, 2002

Related U.S. Application Data

(60) Provisional application No. 60/249,973, filed on Nov. 20, 2000.

(51) Int. Cl.[7] .............................. A61K 9/00; A61K 9/20; A61K 9/28; A61K 31/4458
(52) U.S. Cl. ...................... 424/400; 424/464; 424/467; 514/317
(58) Field of Search ............................... 424/400, 464, 424/467; 514/317

(56) References Cited

U.S. PATENT DOCUMENTS

| | | | |
|---|---|---|---|
| 4,874,793 A | 10/1989 | Franks | |
| 5,284,845 A | 2/1994 | Paulsen | |
| 5,760,095 A | * 6/1998 | White | 514/263.31 |
| 5,885,998 A | 3/1999 | Bencherif et al. | |
| 5,945,123 A | 8/1999 | Hermelin | |
| 6,255,325 B1 | * 7/2001 | Dariani et al. | 514/317 |

OTHER PUBLICATIONS

Brown (in "Placebo for Depression" Neuropsychopharmacology, vol. 10, No. 4, pp. 265–288).*
Diamond, Ivan R., Tannock, Rosemary and Schachar, Russell J. (1998), *Response to Methylphenidate in Children with ADHD and Comorbid Anxiety*, Journal of American Academy of Child and Adolescent Psychiatry, Apr., 1999, 38:4, pp. 402–409.

Conway, Joseph S. (2000), *Placebo and PlaceboEffects in Medicine*, Journal of the Royal Society of Medicine, Jan., 2000, vol. 93, p. 53.
Harper, Phil J. (1999), *The Placebo Effect and the Hidden Benefits of Oral Medicine*, British Journal of Nursing, vol. 8, No. 9, pp. 589–592.
Roberts, Alan H., *The Powerful Placebo Revisited: Magnitude of Nonspecific Effects*, Scripps Clinic and Research Foundation, pp. 35–43.
Klopfer, Bruno (1957), *Psychological Variables In Human Cancer*, Society of Projective Techniques, vol. 21, pp. 331–340.
(1952), *The Bottle of Medicine*, British Medical Journal, Jan. 19, 1952, pp. 149–150.
Balon, Richard (1995), *Placebo for Depression?*, Neuropsychopharmacology, vol. 12, No. 4.
Brown, Walter A. (1994), *Placebo as Treatment for Depression*, Neuropsychopharmacology, vol. 10, No. 4, pp. 265–288.

(List continued on next page.)

Primary Examiner—Thurman K. Page
Assistant Examiner—Blessing Fubara
(74) Attorney, Agent, or Firm—Carter, Schnedler & Monteith (57) ABSTRACT

There is provided a method and associated kit for reducing the normal dosage of a pharmaceutical given to a patient for the treatment of a disorder without substantially reducing its effectiveness. During a first predetermined time period, a substantially full dosage of the pharmaceutical is administered to the patient, preferably with a placebo. During a second predetermined time period, a reduced dosage of the pharmaceutical is administered to the patient, also with a placebo. The second predetermined time period is subsequent to the first predetermined time period. Preferably, the placebo has a distinctive indicia. The placebo, in association with the decreased pharmaceutical, augments the effectiveness of the pharmaceutical by heightening the patient's conditioned response and expectation of effectiveness.

44 Claims, 3 Drawing Sheets

OTHER PUBLICATIONS

Levine, Jon D., Gordon, Newton C., and Fields, Howard L. (1978), *The Mechanism of Place Analgesia*, The Lancet, Sep. 23, 1978, 2, pp. 654–657.

Kirsch, Irving (1985), *Response Expectancy as a Determinant of Experience and Behaviour*, American Psychologist, Nov. 1985, vol. 40, No. 11, pp. 1189–1202.

Horwitz, Ralph I. and Horwitz, Sarah M. (1993), *Adherence to Treatment and Health Outcomes*, Archives of Internal Medicine, Aug. 23, 1993, vol. 153, pp. 1863–1868.

Enserink, Martin (1999), *Can the Placebo Be the Cure?*, Science, 284, pp. 238–240.

(1997), *The Placebo Effect, An Interdisciplinary Exploration*, Harvard University Press, Editor Anne Harrington, Cover Page and Copyright Notice.

Shapiro, Arthur K. and Shapiro, Elaine (1997), *The Placebo: Is It Much Ado about Nothing?*, The Placebo Effect, An Interdisciplinary Exploration, Chapter 1, pp. 12–36.

Spiro, Howard (1997), *Clinical Reflections on the Placebo Phenomenon*, The Placebo Effect, An Interdisciplinary Exploration, Chapter 2, pp. 37–55.

Kirsch, Irving (1997), *Specifying Nonspecifics: Psychological Mechanisms of Placebo Effects*, The Placebo Effect, An Interdisciplinary Exploration, Chapter 8, pp. 166–186.

Conners, C. Keith et al (1996), *Bupropion Hydrochloride in Attention Deficit Disorder with Hyperactivity*, Journal of American Academy of Child and Adolescent Psychiatry, Oct., 1996, 34:10, p. 1314.

\* cited by examiner

THERAPEUTIC PLACEBO ENHANCEMENT OF COMMONLY-USED MEDICATIONS

CROSS-REFERENCE TO PROVISIONAL PATENT APPLICATION

The benefit of U.S. Provisional Patent Application Ser. No. 60/249,973, filed Nov. 20, 2000, is claimed.

BACKGROUND OF THE INVENTION

This invention relates to methods and kits for the treatment of medical disorders.

More particularly, it relates to methods and kits for the treatment of medical disorders utilizing reduced dosages of pharmaceutical without substantially reducing the effectiveness of the treatment.

Placebos (placebo means "I shall please") have always been integral to the healing practices and medicine. In an editorial of the British Medical Journal explicitly recognized the placebo as a legitimate and useful component of medical therapeutics. The rise of the placebo-controlled clinical trial since the 1960's focused attention on the benefits of specific therapies compared with placebo effects. Recent decades of medical research have demonstrated the ubiquitous effects of placebos. Powerful placebo effects have been demonstrated in a range of common medical conditions, including peptic ulcers, irritable bowel, hypertension, low back pain, arthritis, anxiety disorders, depression and ADHD.

The mechanisms of placebo effects are poorly understood. It is known that there are no specific personality predictors of placebo response. Attributes of physicians, including their empathy and sense of confidence, can affect the magnitude of response. Responses to placebo in open trials are generally more robust than in controlled trials. Most importantly, the patient's expectation of improvement powerfully influences the response to placebo.

The results of a clinical trial involving children with Autism of secretin demonstrated no benefit of secretin over placebo. On several of the outcome measures, children in both the placebo and secretin groups showed significant improvement. Other studies of secretin have demonstrated robust placebo responses, including improvements in autistic behaviors and communication.

ADHD is a common condition in children, with estimated prevalence of 3% to 5%. Stimulants are widely used and very effective in the treatment of this condition. The most commonly prescribed stimulant is methylphenidate sold under the trade name Ritalin. Concerns about increasing sales of methylphenidate and potential side effects have generated public debate and controversy about overuse of stimulants.

Methylphenidate is effective in decreasing the symptoms of ADHD in 75% to 80% of children with this condition. Most children respond to a dose of 0.3 to 0.6 mg/kg/dose. At such low to moderate doses, about 10% to 30% of children experience one or more side effects, including loss of appetite, lack of weight gain, irritability, sleep disturbance, nausea or tics. These dose related side effects can be diminished or stopped by decreasing the doses of methylphenidate. Unfortunately, lower doses may be ineffective in treating the symptoms of ADHD.

There is extensive evidence from clinical trials of stimulants showing a robust placebo response in ADHD (Conners et al, 1996; Diamond et al, 1999). It is likely that the effect size is not a constant, but varies among individuals and also over time within individuals. A child who is a clinical responder to methylphenidate may be assumed to have a large component of his/her overall response due to specific effects of methylphenidate and a smaller component due to placebo. Thus it is desirable to take advantage of the "placebo effect" in the treatment of ADHD, as well as other disorders.

OBJECTS OF THE INVENTION

It is, therefore, one object of this invention to provide a method for reducing the normal dosage of a pharmaceutical given to a patient for the treatment of a disorder without substantially reducing the effectiveness the treatment.

It is another object of this invention to take advantage of the placebo effect in reducing the normal dosage of a pharmaceutical without substantially reducing the effectiveness of the treatment.

It is still another object of this invention to provide a method which will take advantage of a patient's conditioned response and expectation of effectiveness in the treatment of a disorder, resulting in a reduction of the pharmaceutical needed for effective treatment.

It is further another object of this invention to provide a treatment of ADHD while reducing potential negative side effects of the treatment.

It is yet another object of this invention to provide a kit used in carrying out the methods stated in the above objects.

SUMMARY OF THE INVENTION

In accordance with one form of this invention, there is provided a method for reducing the normal dosage of a pharmaceutical given to a patient for the treatment of a disorder without substantially reducing its effectiveness. An initial dosage of the pharmaceutical is administered to the patient during a first predetermined time period. A reduced dosage of the pharmaceutical is administered to the patient during a second predetermined time period. The reduced dosage has less pharmaceutical than the initial dosage. The second predetermined time period is subsequent to the first predetermined time period. A placebo is also administered during the second predetermined time period.

In accordance with another form of this invention, there is provided a kit for use in reducing the normal dosage of a pharmaceutical given to a patient for treating a disorder without substantially reducing the effectiveness of the treatment. A container is provided. At least a first unit having a reduced dosage of pharmaceutical is received in the container. At least a second unit having a placebo is also received in the container. Preferably, the kit includes a plurality of first units and a plurality of second units. Also, preferably, the second unit has distinctive indicia. Also, preferably, the kit contains written instructions coordinating the administration of the first and second units. It is also preferred that the patient is informed that the second unit containing the placebo may enhance the treatment of the disorder when taken with the first unit containing the reduced dosage of pharmaceutical.

In accordance with another form of this invention, there is provided a method for reducing the normal dosage of a pharmaceutical given to a patient for the treatment of the disorder without substantially reducing its effectiveness. A substantially normal dosage unit of pharmaceutical is administered during a first predetermined time period. A placebo unit is also administered during the first predetermined time period. A reduced dosage of pharmaceutical is administered during a second predetermined time period. A placebo unit is also administered during the second predetermined time period. The second predetermined time period is subsequent to the first predetermined time period.

It is preferred that a reduced dosage unit is also administered during a third predetermined period which is subsequent to the second predetermined time period. The reduced dosage unit administered during a third predetermined time period has indicia which is substantially the same as the indicia on the placebo unit, so that the patient's conditioned response and expectation of placebo-enhanced effectiveness is maintained.

In accordance with another form of this invention, there is provided a method for reducing the full dosage of a pharmaceutical given to a patient for the treatment of a disorder without substantially reducing its effectiveness by administering a placebo in association with a substantially decreased dosage of the pharmaceutical to enhance the effectiveness of the pharmaceutical, thereby maintaining the effectiveness of the treatment as if the pharmaceutical had been administered at the full dosage level.

In accordance with another form of this invention, there is provided a method for reducing the full dosage of a pharmaceutical given to a patient for the treatment of a disorder without substantially reducing its effectiveness by administering a placebo in a unit bearing distinctive indicia, along with a unit having a full dosage of pharmaceutical, and then administering a placebo in a unit bearing distinctive indicia, along with a unit having a reduced dosage of pharmaceutical, whereby the visible distinctive indicia heightens the patient's conditioned response and expectation of effectiveness.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

DESCRIPTION OF THE PREFERRED EMBODIMENTS

In accordance with the preferred embodiments of the invention, there is provided a method and associated kit for reducing the normal dosage of a pharmaceutical given to a patient for the treatment of a disorder without substantially reducing the effectiveness of the treatment. While the specific research activity with respect to this invention, as discussed below, has been directed to ADHD, it is believed that this invention is applicable to many other disorders. For example, it is believed that the invention is applicable to other common medical conditions, including, but not limited to, peptic ulcers, irritable bowel, hypertension, low back pain, arthritis, anxiety disorders and depression.

In addition, while the only two pharmaceuticals used in connection with the specific research activities with respect to ADHD were methylphenidate and dextroamphetamine, it is believed other pharmaceuticals, specifically central nervous system stimulants, may be used. Of course, other pharmaceuticals would be used in connection with the treatment of disorders other than ADHD, such as those disorders listed above.

Figure 1:
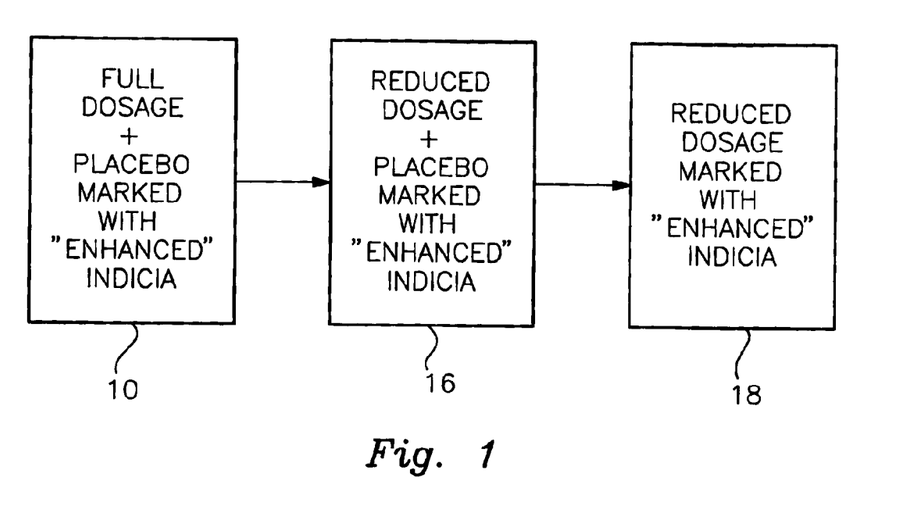
FIG. 1 is a block diagram illustrating one embodiment of the method of the subject invention.
Figure 2:
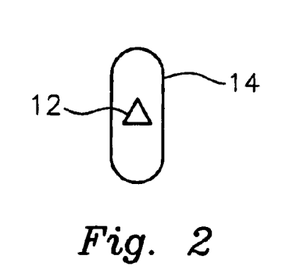
FIG. 2 is a plan view of a pill containing placebo having an enhanced indicia marked thereon.

Referring now more particularly to FIG. 1, a block diagram is shown illustrating a preferred method of the invention. As shown in block 10, a full dosage of the pharmaceutical which, in the case of the treatment of ADHD, may be methylphenidate or dextroamphetamine or salts thereof, is administered to the patient, together with a placebo marked with enhanced indicia, during a first predetermined time period. The enhanced indicia may be the diamond shaped marking 12 on placebo pill 14, as illustrated in FIG. 2. By administering the placebo marked with enhanced indicia, together with the full dosage, it is believed that the patient will associate beneficial effects of the pharmaceutical with the visually distinctive placebo through the repeated pairing of the pharmaceutical and the placebo. Thus the patient will develop a conditioned response to the placebo that is similar to the response the patient has from taken the pharmaceutical. The first predetermined time period may vary. For example, it may be one day or one week. The terms full dosage, normal dosage, and usual dosage are used interchangeably herein to mean the dosage amount given to a patient which is medically appropriate to treat the patient's condition without regard to the dosage reduction technigues taught by this invention.

During a second predetermined time period, as illustrated in block 16, the patient is given a reduced dosage of the pharmaceutical, together with a placebo also marked with enhanced indicia. The second predetermined time period should last at least approximately one week.

Figure 3:
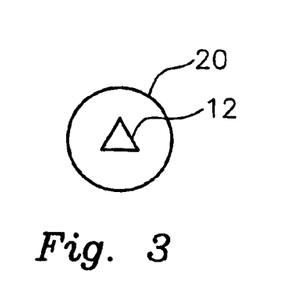
FIG. 3 is a plan view of a pill containing pharmaceutical having an enhanced indicia thereon.

After the second predetermined time period, one may continue the treatment described in block 16, or one may administer a reduced dosage of the pharmaceutical marked with the enhanced indicia, as illustrated in block 18. A reduced dosage pill is illustrated in FIG. 3. Pharmaceutical pill 20 has the diamond shaped enhanced indicia 12 printed thereon, which is identical to the indicia printed on the placebo pill.

It is important to inform the patient before the beginning of the treatment that the pill containing the placebo marked with the enhanced indicia may provide effectiveness when used with the pill containing the reduced dosage pharmaceutical. Thus the visually distinctive placebo heightens both the conditioned response and expectancy effects of the patient.

Figure 4:
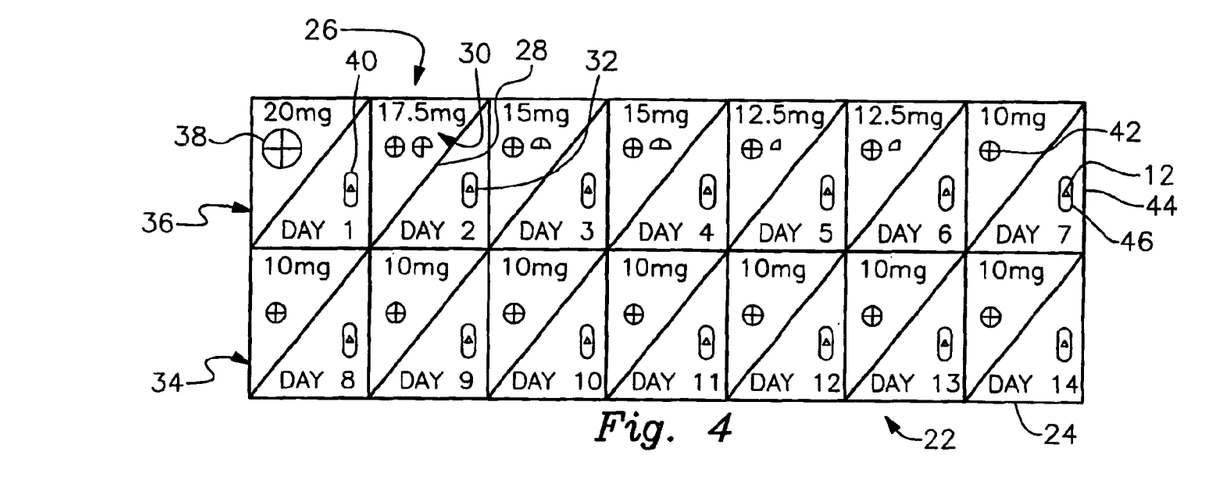
FIG. 4 is a top plan view of a kit illustrating one embodiment of the invention.

The step illustrated in block 16 may include a gradual reduction of the dosage of the pharmaceutical over a time period, such as a one week period. For example, an ADHD patient who has been on 20 mg of methylphenidate per day might receive 17.5 mg on the second day, 15 mg on the third and fourth days, 12.5 mg on the fifth and sixth day, and 10 mg on the seventh day and thereafter. During that one week period, each dosage of the methylphenidate is accompanied with a placebo pill having the enhanced indicia marked thereon. After the fourteenth day, the patient might continue to be given the 10 mg of methylphenidate, together with the placebo pill, or the patient may be converted to a methylphenidate 10 mg pill having the enhanced indicia printed thereon without the need to administer the placebo pill. As illustrated in FIG. 4, the nonstandard dosages during Days 2 and 6 of methylphenidate might be accomplished by breaking off appropriate portions of a 10 mg pill to affect the reduced dosages.

Clinical Study

Twenty-six children with ADHD who were considered to have had a good treatment response to stimulant medication (e.g., methylphenidate) and whose parents were concerned about possible long-term side effects of stimulant treatment for their child were recruited to participate in a study comparing the effects of 50% dose reduction with a placebo "dose enhancer" to the effects of 50% dose reduction alone. Standardized parent and teacher ratings of ADHD behavior, parent ratings of side effects, and clinician ratings of treatment response were taken during each experimental phase. Children were rated as significantly improved during the dose enhancer plus dose reduction condition in terms of both clinician global ratings of improvement and parent ratings of ADHD behavior. Side effects tended to diminish during the dose reduction conditions with no difference between the dose reduction alone and the dose reduction plus dose enhancer conditions. 40% of the children experienced at least a 33% improvement in symptoms during the dose enhancer condition (despite a 50% dose reduction), and 75% of these dose enhancer responders were returned to dose enhancer treatment by their parents at the end of the study.

Subjects were randomly assigned to one of two orders of the experimental conditions set forth below:

(1) BASELINE on current dose of medication of methylphenidate (one week), then 50% DOSE condition in which they received half of their baseline dose (one week), then 50%+DOSE ENHANCER (visually distinctive placebo) condition in which they received half their baseline dose and a dose enhancer pill (one week).

(2) BASELINE on current dose of medication (one week), then 50%+DOSE ENHANCER condition in which they received half their baseline dose and a dose enhancer pill (one week), then 50% DOSE condition in which they received half of their baseline dose (one week).

During the experimental conditions, the child, the parents, and the study Physician were fully aware of the treatment conditions ("open label treatment"), and the parents and child were informed that "the dose enhancer pill may allow you/your child to get the effects of a full dose of your medicine while you only receive half of your dose of medication." The teachers were not informed of the experimental conditions ("single blind treatment"), and thus their ratings were presumed to be "blind" with respect to the different dose manipulations.

Once per week during each phase of these experimental conditions: (a) parents completed the IOWA CONNERS ADHD rating scale, and a stimulant treatment side effects rating scale; (b) the child's primary school teacher completed the IOWA CONNERS ADHD rating scale, and (c) the child was evaluated by the study Physician on the CLINICAL GLOBAL IMPRESSIONS scale. These scales are all standardized instruments for measuring drug treatment effects for children with ADHD.

The resulting data were analyzed by examining each outcome measure (parent IOWA ratings, teacher IOWA ratings, clinician CGI ratings, and parent side effects ratings) separately. Two statistical comparisons (t-test) were made for each measure: (a) a comparison of the 50% dose to the 50% dose+dose enhancer conditions (testing if the addition of the dose enhancer resulted in better treatment during the dose reduction than did dose reduction alone), and (b) a comparison of baseline to the 50% dose condition (testing if dose reduction was associated with a worsening of symptoms).

(1) Parent Behavior Ratings (IOWA Conners Scale)—There was a marginally significant difference (p=0.07) between 50% dose and 50%+Dose Enhancer (means 16.5 and 12.2, respectively) (lower number=less severe symptoms), and there was a marginally significant difference (p=0.08) between Baseline and 50% dose (12.8 and 16.5, respectively). This indicates that ADHD behavior tended to become worse when the dose of stimulant medication was reduced without a dose enhancer (baseline to 50% dose), but that ADHD behavior tended to remain the same when the dose of stimulant medication was reduced with the dose enhancer. This suggests that the dose enhancer can provide adequate symptom control during a period of dose reduction.

(2) Teacher Behavior Ratings (IOWA Conners Scale)—There were no significant differences between conditions; means—Baseline=9.5, 50% dose=8.9, 50%+Dose Enhancer=10.0 (lower number=less severe symptoms). This indicates that when not informed of changes in their student's dose of stimulant medication, teachers do not observe a change in their student's ADHD behavior. It further indicates that the dose reduction+dose enhancer condition did not results in a worsening of ADHD symptoms as reported by teachers.

(3) Side Effects Rating Scale—There were no significant differences between conditions. Baseline (mean=7.3) was higher than both 50% dose (5.6) and 50%+Dose Enhancer (5.05) (lower number means less severe symptoms). This indicates that children were exhibiting some stimulant-related side effects while on their regular dose, and that the severity of these symptoms decreased when the dose was reduced by half.

(4) Clinical Global Impressions Scale—There was a significant difference (p=0.004) between the 50% dose and the 50%+Dose Enhancer conditions (means 12.9 and 11.0, respectively) (lower number=larger improvement in symptoms+less side effects relative to baseline). This indicates that when considering the combination of treatment positive effects and drug-related side effects, children tended to do better overall during the dose enhancer condition.

(5) Individual Subject Analysis—

A "responder" to the Dose Enhancer was defined as at least 33% reduction in parent behavior ratings coupled with no worsening in either teacher ratings or side effects during the dose enhancer phase. Eight subjects (40% of final sample) met criteria for responder. Of these responders, all had a trend of reduced side effects during the dose enhancer phase with four/eight reporting large reductions in side effects. Of these responders, six had essentially no change in teacher reported behavior ratings, and two showed a reduction in teacher reported behavior ratings. Responder/Nonresponder status did not correlate with age, gender, stimulant type, baseline dose, or baseline side effects rating.

Approximately half of the children who underwent dose reduction with a dose enhancer demonstrated no noticeable deterioration as rated by teachers AND were also reported as BETTER by their parents in terms of both behavior and side effects.

The Kit

Figure 5:
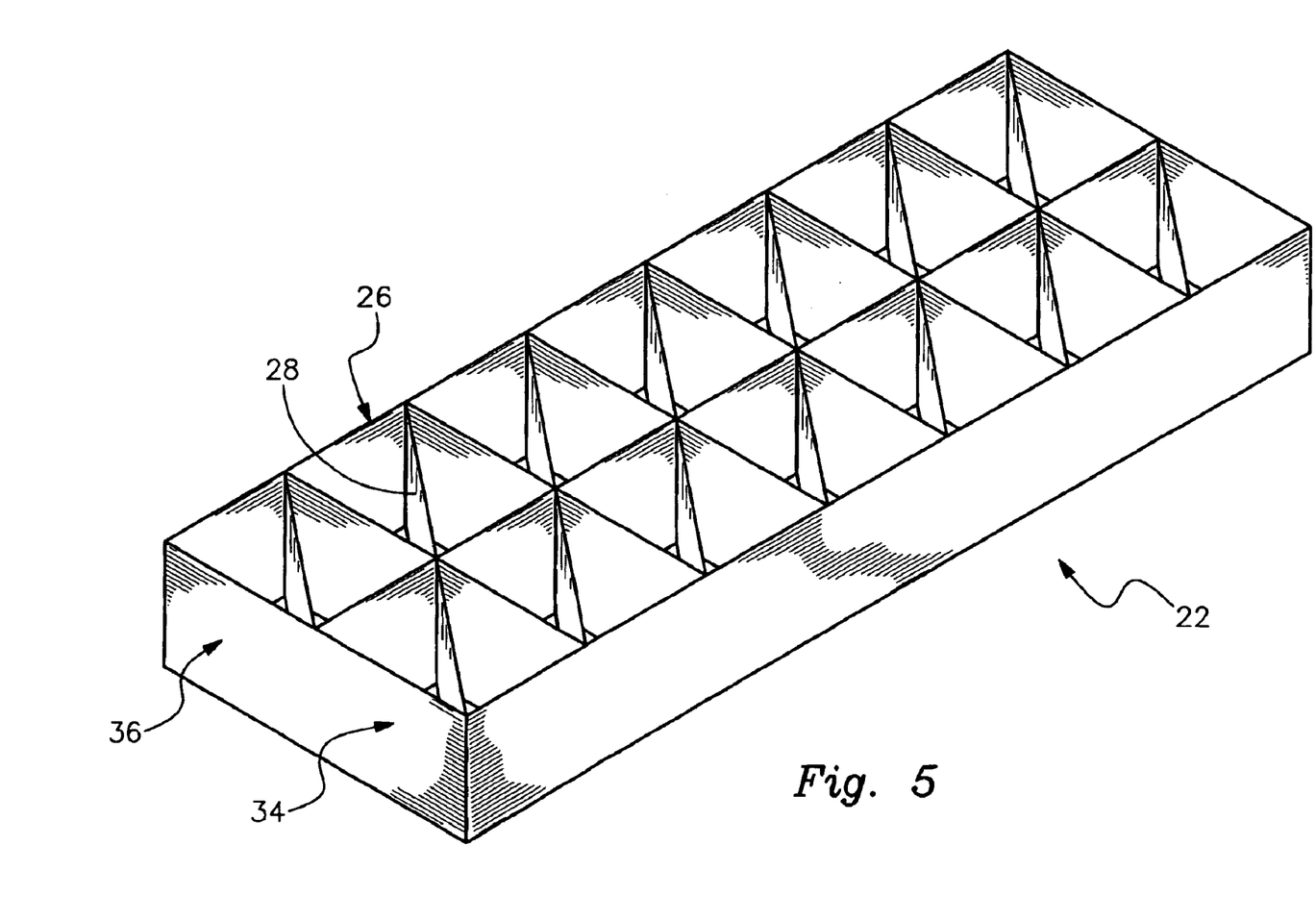
FIG. 5 is a perspective view of the kit of FIG. 4, however with the pills having been removed and omitting the dosage amount and day legends.

Referring now more particularly to FIGS. 4 and 5, there is provided kit 22 for providing the dose reduction treatment discussed above. The kit 22 includes an elongated container 24. A plurality of sub-compartments arranged in rows are provided for receiving pharmaceutical pills and placebo pills. Each sub-compartment, such as sub-compartment 24, is subdivided by a diagonal divider 28 and the pharmaceutical pill(s) 30 are placed on one side of subdivider 28 and the placebo pill 32 is placed on the other side of subdivider 28, all within the same sub-compartment 26.

Figure 6:
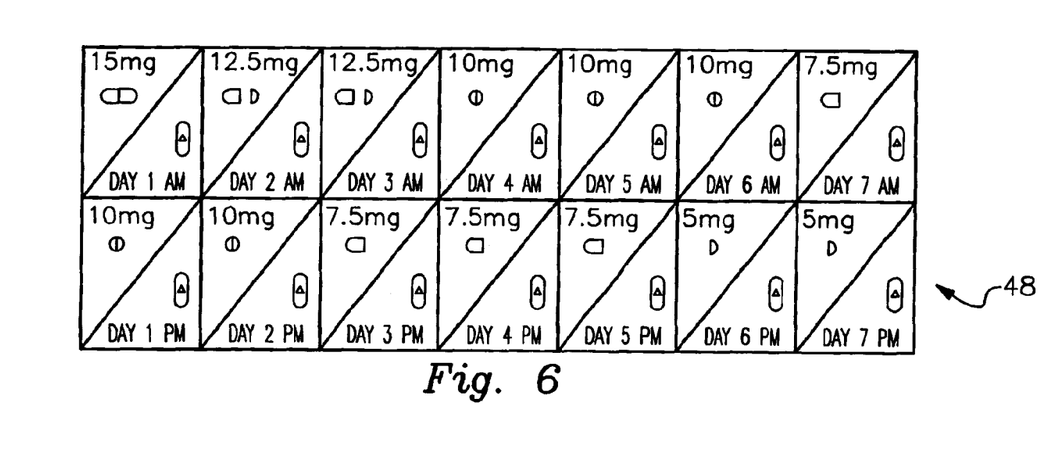
FIG. 6 is a top plan view of a kit illustrating another embodiment of the invention.

The kits illustrated in FIGS. 4, 5 and 6 contain two columns and seven rows of sub-compartments. Each sub-compartment is a row which represents a day. However, other combinations of rows and columns of sub-compartments can be utilized. For example, the kit may comprise sub-compartments in a seven by four matrix to accommodate different dosage or reduction treatments. As illustrated in FIGS. 4 and 6, each sub-compartment may have a particular day printed or embossed thereon. In addition, each sub-compartment may have the strength of the pharmaceutical printed or embossed thereon for each individual day.

In the example of the kit 22 shown in FIG. 4, the patient is on methylphenidate 20 mg for the first day. Over the course of one week, the dosage is gradually decreased to 10 mg. The kit may be used for additional weeks to maintain the patient on this lower dose to ensure that the clinical effect is maintained. In kit 48 shown in FIG. 6, which is substantially the same as the kit of FIG. 4, except for the type of stimulant and the frequency of medication and placebo given per day, the patient is on dextroamphetamine 15 mg (oval) in the morning and 10 mg (round) in the afternoon for the first day. Using half tablets of these two doses (7.5 mg and 5 mg, respectively), the doses are decreased over the course of one week to 50% of the original dose. The kit of FIG. 6 could also be used to maintain these lower doses for an additional week, however, two additional columns of sub-compartments would be needed.

Each kit should include written instructions to coordinate the administration of the pharmaceutical containing pills and placebo containing pills. These instructions provide the dosage of stimulant therapy the patient should take during the dose reduction. For example, with the kit of FIG. 4, the instructions state that on Day 1, the patient takes the usual doses of stimulant from sub-compartment 36. In this case, the stimulant is a 20 mg pill of methylphenidate, illustrated by pill 38. In addition, on the first day, the patient will take the so-called dose enhancer which is placebo pill 40, which is in sub-compartment 36, and as illustrated in FIG. 4. The dosage of the stimulant will be reduced during the remainder of the week until it reaches 10 mg on Day 7. That is, the patient takes the 10 mg pill 42 which is within sub-compartment 44, as well as the placebo pill 46 bearing the enhanced indicia 12.

After the second week, as illustrated in row 34, where a patient takes a 10 mg pill of stimulant, as well as the placebo pill having enhanced indicia, the physician may have the patient take a 10 mg pill of stimulant with the enhanced indicia 12 marked thereon, as illustrated in FIG. 3 for the remainder of the therapy.

In addition, the patient should be informed by the written instructions and/or by the physician that the pill containing the placebo may enhance the treatment of the patient's disorder when taken with the pill containing the pharmaceutical.

Specifically in the treatment of ADHD, a physician prescribes a dose reduction kit, such as a kit shown in FIGS. 4–6, to help the patient onto a lower dose of stimulant therapy for ADHD. The patient is informed that this will involve the taking of a dose enhancer with each dose of stimulant that the patient takes. The physician may inform the patient that the dose enhancer is a small pill containing no active drug and is entirely harmless, and the patient should be informed that the pill containing the placebo may enhance the effectiveness of the stimulant drug.

Using this kit, the patient achieves a 50% reduction in stimulant while maintaining the desired effects of the stimulant in the treatment of ADHD.

From the foregoing description of the preferred embodiment of the invention, it will be apparent that many modifications may be made therein. It should be understood, however, that this embodiment of the invention is an exemplification of the invention only and that the invention is not limited thereto. It is to be understood, therefore, that it is intended in the appended claims to cover all modifications as fall within the true spirit and scope of the invention.

What is claimed is:

1. A method for reducing the normal dosage of a pharmaceutical taken from the group consisting essentially of methylphenidate and dextroamphetamine and salts thereof given to a patient for the treatment of a disorder without substantially reducing its effectiveness comprising the steps of:

administering an initial dosage of the pharmaceutical during a first predetermined time period;

administering a reduced dosage of the pharmaceutical a second predetermined time period; said reduced dosage having less pharmaceutical than said initial dosage; said second predetermined time period being subsequent to said first predetermined time period;

administering a placebo substantially contemporaneously with the administration of said reduced dosage during said second predetermined time period.

2. A method as set forth in claim 1, further including the step of administering a placebo during said first predetermined time period.

3. A method as set forth in claim 1, wherein said reduced dosage is administered in a first unit and said placebo is administered in a second unit.

4. A method as set forth in claim 3, wherein said second unit has a distinctive indicia.

5. A method as set forth in claim 4, wherein said reduced dosage and said placebo are administered in a common unit.

6. A method as set forth in claim 5, wherein said common unit has indicia which is substantially identical to said indicia on said second unit.

7. A method as set forth in claim 1, further including the step of informing the patient during or prior to the second predetermined time period that said placebo does not contain said pharmaceutical.

8. A method as set forth in claim 1, further including the step of informing the patient that the placebo may provide effectiveness when used with said pharmaceutical.

9. A method as set forth in claim 1, wherein said initial dosage is a normal dosage.

10. A method as set forth in claim 1, further including the step of administering a reduced dosage during a third predetermined time period; said placebo not being administered during said third predetermined time period.

11. A method as set forth in claim 10, wherein said reduced dosage administered during said third predetermined time period is contained in units having an indicia which is substantially the indicia associated with said placebo.

12. A method as set forth in claim 4, wherein said indicia enables the patient to expect the effects of said initial dosage.

13. A method as set forth in claim 1, further including the step of gradually lowering the dosage of said pharmaceutical from said initial dosage at the end of said first predetermined time period to said reduced dosage during said second predetermined time period, and administering said placebo during said steps of gradually reducing the dosage of the pharmaceutical.

14. A method as set forth in claim 1, wherein said pharmaceutical is stimulant.

15. A method as set forth in claim 14, wherein said stimulant is a central nervous system stimulant.

16. A method as set forth in claim 15, wherein said pharmaceutical is methylphenidate.

17. A method as set forth in claim 15, wherein said pharmaceutical is dextroamphetamine or salt thereof.

18. A method as set forth in claim 14, wherein the disorder treated is ADHD.

19. A kit for use in reducing the normal dosage of a pharmaceutical taken from the group consisting essentially of methylphenidate and dextroamphetamine and salts thereof given to a patient for treating a disorder without reducing its effectiveness comprising:
a container;
at least a first unit having a reduced dosage of said pharmaceutical;
at least a second unit having a placebo;
said first and second units received in said container; said first and second units adapted to be substantially contemporaneously taken by the patient.

20. A kit as set forth in claim 19, further including a plurality of first units and a plurality of second units.

21. A kit as set forth in claim 20, wherein said container includes a plurality of sub-compartments; said sub-compartments arranged in columns and rows; said plurality of first units and said plurality of second units received in said sub-compartments.

22. A kit as set forth in claim 21, wherein each sub-compartment includes a divider which divides each sub-compartment into substantially two halves; a first unit received in one half of a substantial number of said sub-compartments, and a second unit received in the other half of a substantial number of said sub-compartments.

23. A kit as set forth in claim 19, wherein said first and second units are pills.

24. A kit as set forth in claim 19, further including written instructions coordinating the administration of said first and second units, whereby said first and second units will work together in treating the disorder.

25. A kit as set forth in claim 19, wherein said second unit has distinctive indicia.

26. A kit as set forth in claim 20, further including a plurality of higher dosage units; said higher dosage units containing more of the pharmaceutical then said first unit.

27. A kit as set forth in claim 26, further including written instructions coordinating the administration of said first, second and higher dosage units, whereby said higher dosage units and a first portion of said second units will be administered during a first predetermined time period, and said first unit and a second portion of said second units will be administered during a first predetermined time period; said first predetermined time preceding said second predetermined time period.

28. A kit as set forth in claim 24, wherein said written instructions indicate to the patient that the second unit containing the placebo may enhance the treatment of the disorder when taken with the first unit containing the reduced pharmaceutical.

29. A kit as set forth in claim 28, further including a third unit; said third unit containing a reduced dosage of pharmaceutical and a placebo; said third unit to be administered subsequent to said first and second units; said third unit having substantially similar indicia as said second unit.

30. A method for reducing the normal dosage of a pharmaceutical taken from the group consisting essentially of methylphenidate and dextroamphetamine and salt thereof given to a patient for the treatment of a disorder without substantially reducing its effectiveness comprising the steps of:
administering substantially the normal dosage unit of a pharmaceutical during a first predetermined time period;
administering a placebo substantially contemporaneously with the administration of said normal dosage unit during said first predetermined time period;
administering a reduced dosage unit of pharmaceutical during a second predetermined time period;
administering a placebo unit substantially contemporaneously with the administration of said reduced dosage during said second predetermined time period; said second predetermined time period being subsequent to said first predetermined time period.

31. A method as set forth in claim 30, wherein each of said placebo units has distinguishing indicia.

32. A method as set forth in claim 30, further including the step of administering a reduced dosage unit during a third predetermined time period; said third predetermined time period being subsequent to said second predetermined time period.

33. A method as set forth in claim 32, wherein said third predetermined unit has indicia which is substantially the same as indicia on said placebo unit.

34. A method as set forth in claim 30, further including the step of informing the patient during or prior to said first predetermined time period that said placebo unit does not contain said pharmaceutical.

35. A method as set forth in claim 30, further including the step of informing the patient that said placebo unit may be effective in treating the disorder when used with said reduced dosage unit.

36. A method as set forth in claim 30, further including the step of gradually lowering the dosage of said pharmaceutical and administering said placebo while gradually reducing the dosage of said pharmaceutical.

37. A method as set forth in claim 30, wherein said pharmaceutical is a stimulant.

38. A method as set forth in claim 37, wherein said pharmaceutical is a central nervous system stimulant.

39. A method as set forth in claim 38, wherein said pharmaceutical is methylphenidate.

40. A method as set forth in claim 38, wherein said pharmaceutical is a dextroamphetamine or salts thereof.

41. A method as set forth in claim 30, wherein said disorder treated is ADHD.

42. A method for reducing the full dosage of a pharmaceutical taken from the group consisting essentially of methylphenidate and dextroamphetamine and salts thereof given to a patient for the treatment of a disorder without substantially reducing its effectiveness comprising the steps of:
administering a placebo in association with a substantially decreased dosage of said pharmaceutical to augment the effectiveness of the pharmaceutical, thereby maintaining the effectiveness of said pharmaceutical at the full dosage level; said placebo being administered substantially contemporaneously with the administration of said decreased dosage.

43. A method for reducing the full dosage of a pharmaceutical taken from the group consisting essentially of methylphenidate and dextroamphetamine and salts thereof given to a patient for the treatment of a disorder without substantially reducing its effectiveness comprising the steps of:

administering a placebo in a unit bearing a visibly distinctive indicia along with a unit having a full dosage of said pharmaceutical;

administering a placebo in a unit bearing said visibly distinctive indicia along with a unit having a reduced dosage of said pharmaceutical, whereby the visibly distinctive indicia heightens the patient's conditioned response and expectation of effectiveness.

44. A method as set forth in claim 43, further including the step of:

administering a reduced dosage of said pharmaceutical in a unit bearing said distinctive indicia subsequent to the step of administering said placebo along with the reduced dosage.

* * * * *